United States Patent
Kanuka et al.

(10) Patent No.: US 7,942,832 B2
(45) Date of Patent: May 17, 2011

(54) MEDICAL GUIDE WIRE

(75) Inventors: Satoru Kanuka, Fujinomiya (JP);
Chikei Shinohara, Fujinomiya (JP);
Akihiko Umeno, Fujinomiya (JP);
Noriyuki Tamai, Numazu (JP); Yutaka Tano, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 881 days.

(21) Appl. No.: 11/261,533

(22) Filed: Oct. 31, 2005

(65) Prior Publication Data
US 2006/0116609 A1 Jun. 1, 2006

(30) Foreign Application Priority Data

Nov. 1, 2004 (JP) .................................. 2004-317821
Oct. 6, 2005 (JP) .................................. 2005-294010

(51) Int. Cl.
*A61M 25/00* (2006.01)
(52) U.S. Cl. ...................................................... 600/585
(58) Field of Classification Search .............. 604/523, 604/164.01, 164.13, 264, 528, 93.01; 600/585
See application file for complete search history.

(56) References Cited

U.S. PATENT DOCUMENTS

| | | | |
|---|---|---|---|
| 4,779,628 A | 10/1988 | Machek | |
| 4,854,330 A * | 8/1989 | Evans et al. | 600/585 |
| 4,886,067 A * | 12/1989 | Palermo | 600/434 |
| 4,971,490 A * | 11/1990 | Hawkins | 600/585 |
| 5,001,825 A * | 3/1991 | Halpern | 29/456 |
| 5,095,915 A * | 3/1992 | Engelson | 600/585 |
| 5,385,152 A * | 1/1995 | Abele et al. | 600/585 |
| 5,599,492 A * | 2/1997 | Engelson | 264/167 |
| 5,836,893 A | 11/1998 | Urick | |
| 6,132,389 A * | 10/2000 | Cornish et al. | 600/585 |
| 6,139,540 A * | 10/2000 | Rost et al. | 600/585 |
| 6,251,085 B1 * | 6/2001 | Tezuka | 600/585 |
| 6,254,550 B1 * | 7/2001 | McNamara et al. | 600/585 |
| 2001/0009981 A1 | 7/2001 | DuBois et al. | |
| 2002/0151823 A1 * | 10/2002 | Miyata et al. | 600/585 |
| 2003/0229298 A1 | 12/2003 | Iwami et al. | |
| 2004/0073141 A1 * | 4/2004 | Hartley et al. | 600/585 |
| 2005/0080356 A1 * | 4/2005 | Dapolito et al. | 600/585 |
| 2005/0131316 A1 * | 6/2005 | Flagle et al. | 600/585 |
| 2005/0159725 A1 * | 7/2005 | Tockman et al. | 604/500 |
| 2006/0264784 A1 * | 11/2006 | Lupton | 600/585 |

FOREIGN PATENT DOCUMENTS

| | | |
|---|---|---|
| GB | 2 064 963 A | 6/1981 |
| JP | 2004-181184 | 7/2004 |
| JP | 2004181184 A * | 7/2004 |

* cited by examiner

*Primary Examiner* — Max Hindenburg
*Assistant Examiner* — Jonathan M Foreman
(74) *Attorney, Agent, or Firm* — Buchanan Ingersoll & Rooney PC

(57) ABSTRACT

A medical guide wire includes a core wire having a distal portion, and a cover portion formed of a resin for covering at least the distal portion of the core wire, and is provided with a distal shape portion having a curved portion, wherein the distal portion of the core wire includes a tapered portion continuously varied in outside diameter, and a distal flexible portion provided on the distal side of the tapered portion, and the wire diameter variation rate at the tapered portion is 40 to 55%.

17 Claims, 11 Drawing Sheets

MEDICAL GUIDE WIRE

BACKGROUND OF THE INVENTION

The present invention relates to a medical guide wire for use in a process in which a medical implement such as a catheter and an introducer kit used for the purpose of treatment or diagnosis is introduced to a desired site in a blood vessel.

A medical guide wire is used in introducing a medical implement, such as a catheter and an introducer sheath, into a blood vessel and leaving the implement indwelling in the blood vessel, at the time of percutaneously diagnosing and/or treating a blood vessel. The location through which to introduce the medical implement such as catheter into the blood vessel has hitherto been mainly femoral (thigh), but has been being changed in recent years to brachial (arm), particularly radial (wrist), for alleviating the burden on the patient. As a result, a medical guide wire provided at its distal portion with a J shape, for example, is being desired which can be used safely in the radial and the brachial blood vessels tending to be branched or meander and is excellent in steerability.

Conventionally, at the time of inserting a medical guide wire having a J shape at its distal portion into a guide needle, a catheter or the like, an assisting implement (an inserter, or a straightener) for facilitating the insertion has been used. Particularly in the case where the radius of curvature of the J-shaped curved portion is small, however, it has been needed to withdraw the guide wire from the blood vessel and re-insert the guide wire into the inserter in such occasions as exchange of the catheter.

SUMMARY OF THE INVENTION

The present invention provides a medical guide wire including a core wire having a distal portion, and a cover portion formed of a resin for covering at least the distal portion of the core wire, the guide wire provided with a distal shape portion having a curved portion, wherein the distal portion of the core wire includes a tapered portion continuously varied in outside diameter, and a distal flexible portion provided on the distal side of the tapered portion, and the wire diameter variation rate at the tapered portion is 40 to 55%.

It is preferable that the distal flexible portion is substantially circular in cross section, and the diameter thereof is 0.08 to 0.13 mm. The distal flexible portion is preferably more flexible than the tapered portion. The distal flexible portion is preferably flat in cross section. It is preferable that the taper at the distal portion of the core wire has a start portion and an end portion and that the taper start portion is located at the curved portion of the distal shape portion. The flexural strength at 30 mm to the proximal side from a most protruding position of the distal shape portion is preferably not less than 1.5 gf. The spreading load of the distal shape portion is preferably not more than 15 gf. The radius of curvature of the distal shape portion is preferably 1 to 3 mm. The opening angle of the distal shape portion is preferably 0 to 30°. The length of the distal flexible portion is preferably 8 to 15 mm.

The surface of the cover portion on at least the inside of the curved portion is preferably provided with a groove substantially orthogonal to the axial direction. The groove is preferably annular or spiral in shape. The groove is preferably provided along the whole circumference of the surface of the cover portion at the curved portion. The groove is preferably provided only in the surface of the cover portion at the curved portion. A slit is preferably provided in place of the groove. The groove is preferably wavy in longitudinal section.

The thickness in the direction of the radius of curvature, of the core wire at the curved portion, is preferably smaller than the thickness in the direction orthogonal to the radius-of-curvature direction. It is preferable that the core wire at the distal flexible portion is substantially circular in cross section. Preferably, the cross-sectional area of the core wire at the curved portion is roughly equal to the cross-sectional area of the core wire at the distal flexible portion. The cover portion at the core wire at the curved portion is preferably flat in cross section.

It is preferable that, in the distal shape portion, the cross-sectional center point of the core wire and the cross-sectional center point of the cover portion are located at different positions. The cross-sectional center point of the cover portion is preferably deviated to the outside in a radius-of-curvature direction of the curved portion relative to the cross-sectional center point of the core wire. Preferably, the cross-sectional center point of the cover portion is located inside the cross section of the core wire. Alternatively, the cross-sectional center point of the cover portion is located outside the cross section of the core wire.

The present invention provides a medical guide wire comprising a core wire having a distal portion, and a cover portion formed of a resin for covering at least said distal portion of said core wire, said guide wire provided with a distal shape portion having a curved portion, wherein said distal portion of said core wire comprises a tapered portion continuously varied in outside diameter and having a start portion being located at said curved portion of said distal shape portion and an end portion, and a distal flexible portion provided on the distal side of said tapered portion. The start portion is preferably located at an apex of said curved portion.

DETAILED DESCRIPTION OF THE PREFERRED EMBODIMENTS

Figure 1:
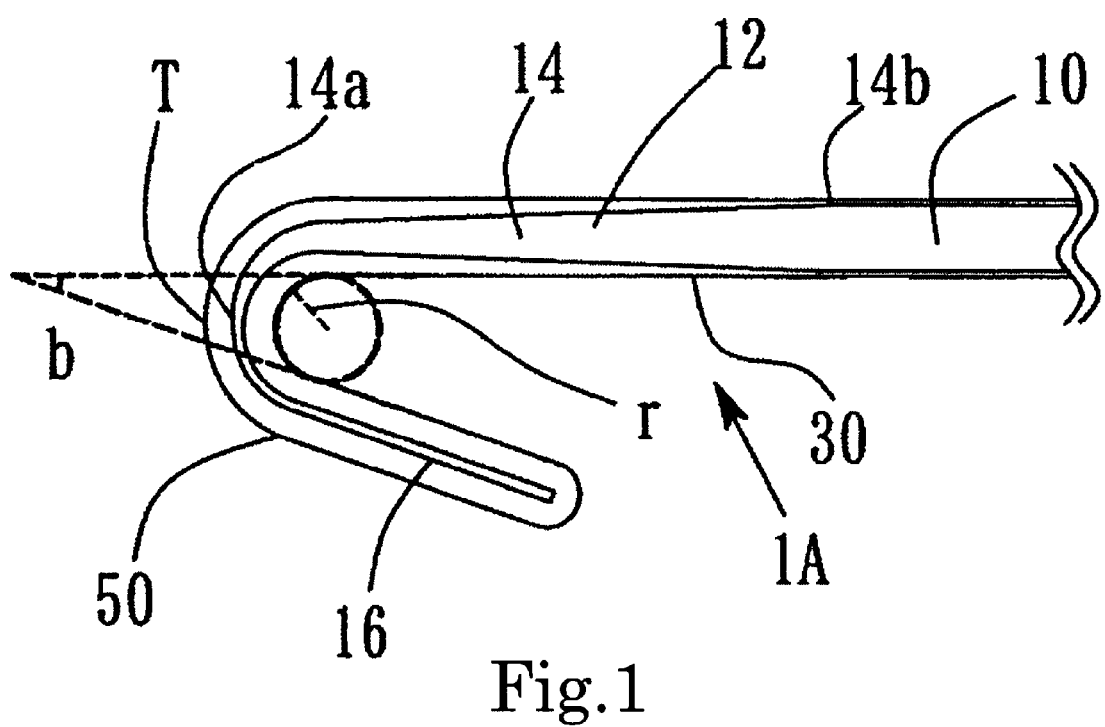
FIG. 1 is a sectional view showing one embodiment of the medical guide wire according to the present invention.
Figure 2:
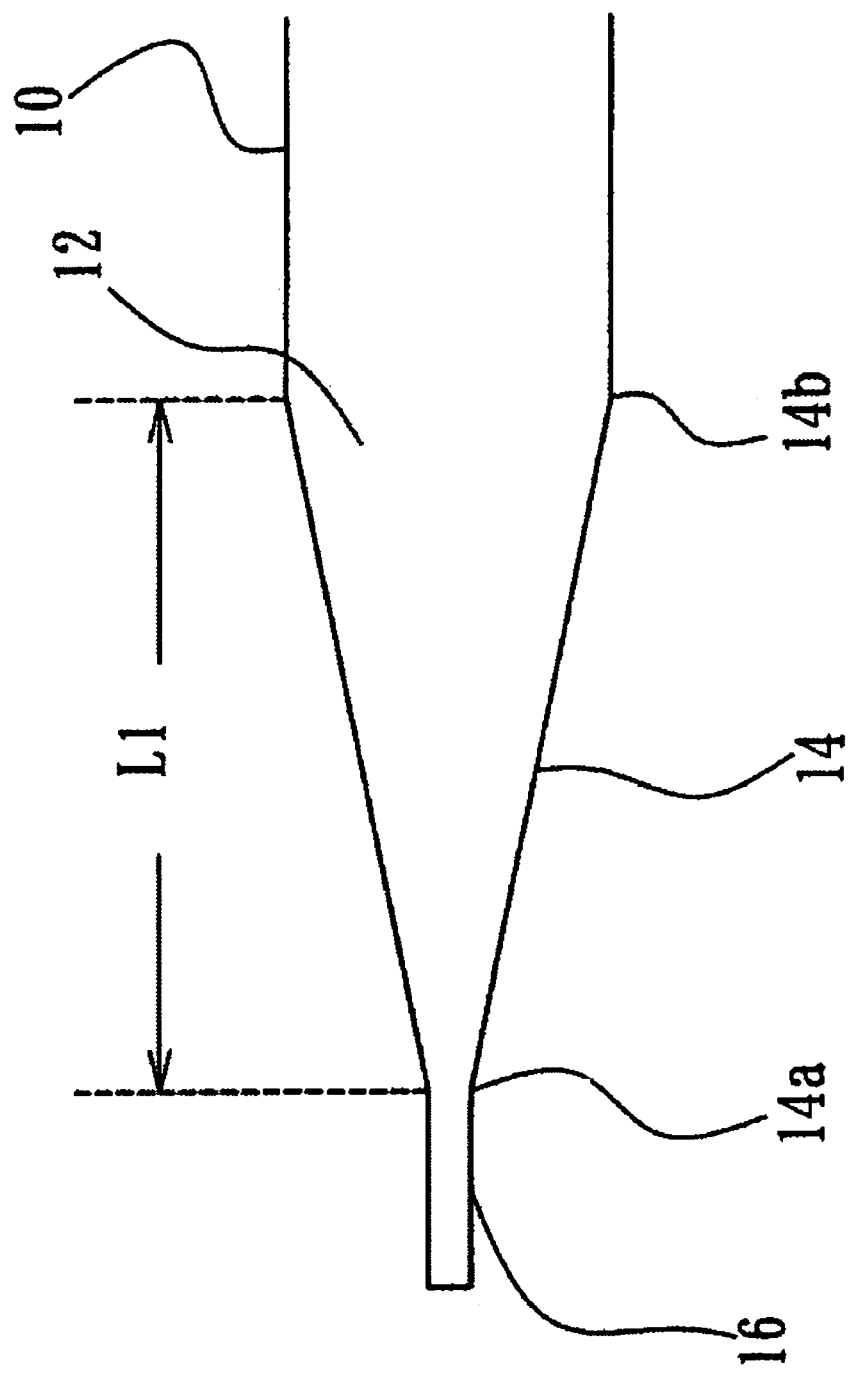
FIG. 2 is a side view showing a core wire in a medical guide wire according to the present invention.

FIG. 1 is a sectional view showing one embodiment of a medical guide wire according to the present invention, and FIG. 2 is a side view showing a core wire in the medical guide wire according to the present invention. The core wire in FIG. 2 is depicted a linear shape in order to easily understand a wire diameter variation rate in detail below. Now, description will be made below referring to the medical guide wire 1A which is one embodiment of the present invention. As shown in FIG. 1, the guide wire 1A includes a core wire 10 having a distal portion 12, and a cover portion 30 formed of a resin for covering at least the distal portion 12 of the core wire 10. The guide wire 1A is provided with a distal shape portion 50 having a curved portion. As shown in FIG. 2, the distal portion 12 of the core wire 10 is provided with a tapered portion 14 continuously varied in outside diameter, and a distal flexible portion 16 provided on the distal side of the tapered portion 14. The tapered portion 14 has a taper start portion 14a at which the increase in outside diameter toward the proximal side is started, and a taper end portion 14b at which the increase in outside diameter ends.

The rate of variation in wire diameter (wire diameter variation rate) in the present invention is determined as follows. As shown in FIG. 2, let the outside diameter at the taper start portion 14a be $\phi 1$ (mm), let the core outside diameter at the taper end portion 14b be $\phi 2$ (mm), and let the length from the taper start portion 14a to the taper end portion 14b be L (cm), the wire diameter increase rate $\alpha$ of the tapered portion 14 is determined as $(((\phi 2 - \phi 1)/\phi 1) \times 100)/L$, i.e., determined as wire diameter increase rate per 1 cm. In the present invention, $\alpha$ is 40 to 55%, preferably 45 to 50%. If $\alpha$ is less than 40%, the position of holding the guide wire in the beginning stage of insertion into a catheter or the like is located on the distal side relative to the taper end portion 14b, and frequent re-holding is needed. Therefore, a burden is exerted on the user in the operation of inserting the guide wire into a catheter or the like. When a portion near the distal portion of the guide wire is held, it is highly possible that the holding might influence a lubricant coating on the surface of the guide wire or that, depending on the blank material of the core wire, the holding with an excessively strong force might give an unrecoverable bend to the core wire. On the other hand, if a exceeds 55%, steerability in the catheter is poor, though the insertability tends to be enhanced. Besides, it is possible that the core wire would be broken when the guide wire distal portion is trapped in a blood vessel.

The core wire 10 in the medical guide wire according to the present invention has an outside diameter of 0.33 to 0.82 mm. The distal flexible portion 16 of the core wire 10 is roughly circular in cross section, and the outside diameter thereof is preferably 0.08 to 0.13 mm, more preferably 0.08 to 0.12 mm. In many cases, the core wire 10 is operated with its distal portion opened, in a catheter or a small-diameter blood vessel. In recent years, there has been a tendency that, if the outside diameter of the distal flexible portion 16 of the core wire 10 is greater than 0.13 mm, the use of such a guide wire is evaded by a physician on the ground that "the distal portion is too hard (stiff) to use the guide wire easily". Where the outside diameter of the distal flexible portion 16 of the core wire 10 is smaller than 0.08 mm, it is difficult to produce the core wire 10, though the flexibility of the distal portion is enhanced. In addition, the distal flexible portion 16 is so weak against tensile loads that this portion would highly expectedly broken in a living body in the practical use of the guide wire, which naturally is unfavorable. The distal flexible portion 16 may have a flat shape such as a rectangular shape and an oblong (elliptic) shape in cross section. Since the distal flexible portion 16 is more flexible than the tapered portion 14, the possibility of damaging a blood vessel is lowered, even where the distal flexible portion 16 goes precedingly in the blood vessel.

The length of the distal flexible portion 16 of the core wire 10 is preferably 8 to 15 mm, more preferably 11 to 15 mm. With the length of the distal flexible portion 16 in this range, it is difficult for the guide wire 1A to erroneously enter into a blood vessel branch, particularly in a lower arm portion, and it is difficult for the distal portion of the guide wire 1A to scratch the blood vessel wall. In addition, the distal flexible portion 16 has a circular cross section with an outside diameter substantially constant along the length direction thereof, but may become gradually slenderer toward the distal portion, as indicated by the guide wire 1B in FIG. 3. Where the distal flexible portion 16 is made to be gradually slenderer, when the guide wire is fed forward in a blood vessel with the distal shape portion 50 spread, the tipmost portion of the guide wire is the most flexible, so that the effect of preventing damage to the blood vessel inside wall can be further enhanced. Where the distal flexible portion 16 becomes gradually slenderer toward the distal portion, the rate of variation in outside diameter thereof is preferably smaller than the wire diameter increase rate $\alpha$. In the case where the distal flexible portion 16 is flat in cross section, it is preferably that the cross-sectional area is gradually reduced toward the distal portion. While the distal flexible portion 16 is rectilinear in FIG. 1, it may be curved in a direction different from the direction of curvature of the distal shape portion 50. For example, the distal flexible portion 16 is preferably curved to the side opposite to the side to which the distal shape portion 50 is curved. The distal flexible portion 16 may be curved toward a three-dimensional direction.

The medical guide wire 1A is provided with the distal shape portion 50 having a curved portion. Examples of the shape of the distal shape portion 50 include not only the shape so-called "J type" as shown in FIG. 1 but also a beak-like shape, and a combined shape of the J type and the angle type. With the distal shape portion 50 thus provided, even when the distal portion of the guide wire touches against the blood vessel inside surface, forces are broken up so that the influence of the touching is restrained.

The taper start portion 14a of the distal portion 12 of the core wire 10 in the medical guide wire 1A is preferably located in the curved portion of the distal shape portion 50, preferably located in the vicinity of the position corresponding to the most projected portion (apex T of the J curved shape) when viewed from the proximal side toward the distal side, as shown in FIG. 1. At the time of inserting the guide wire into a catheter or the like, it is necessary for the J shape to be spread and extended. In this case, with the hardness of the curved portion (distal shape portion 50) such as a J-shaped portion provided with an appropriate anisotropy, it is possible to realize both a high flexibility (spreadability) on the distal side and a strong flexural strength (pushability) on the proximal side.

In other words, where the taper start portion 14a is located on the proximal side relative to the curved portion such as a J-shaped portion, the hardness (stiffness) of the shaped portion is substantially uniform (isotropic). Therefore, the flexural strength on the proximal side is insufficient, so that the curved portion does not contribute much to improvement in insertability into a catheter or the like. On the other hand, where the taper start portion 14a is located on the distal side relative to the curved portion of the J shape, the force required for spreading the J-shaped portion (the spreading load on the distal shape portion) may be enlarged.

With the taper start portion 14a of the distal portion 12 of the core wire 10 provided in the curved portion of the distal shape portion 50, the flexural strength on the proximal side is made the most of, so that insertability into a catheter or the like is improved. In addition, since the force necessary for spreading the J-shaped portion (the spreading load on the distal shape portion) may be small, it is easier for the guide wire to pass through the small lumen of a catheter or the like; in addition, where the distal portion is hooked on a branch blood vessel at the time of withdrawing the guide wire from the blood vessel, the load exerted on the guide wire at the time of release from the branch portion is small, so that the influence on the branch portion is little.

With the taper start portion 14*a* of the distal portion 12 of the core wire 10 provided in the curved portion of the distal shape portion 50, the wire diameter variation rate at said tapered portion may be 35 to 55%, more preferably 40 to 55%, and more preferably 45 to 50%. 40 to 55%

The distal shape portion 50 of the core wire 10 is provided with a portion at which the cross-sectional area of the core wire 10 is gradually reduced toward the distal portion, as shown in FIG. 1.

Figure 3:
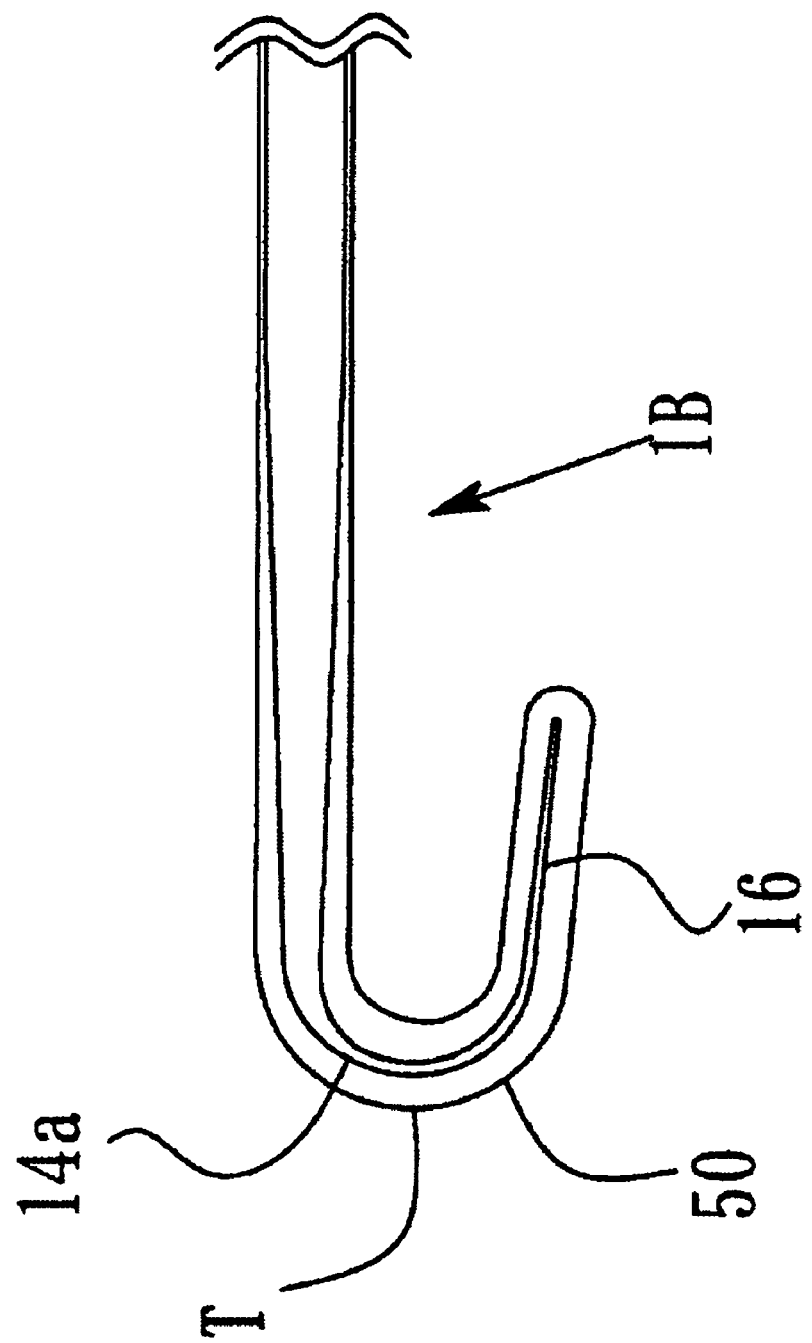
FIG. 3 is a cross-sectional view showing another embodiment of the medical guide wire according to the present invention.
Figure 4:
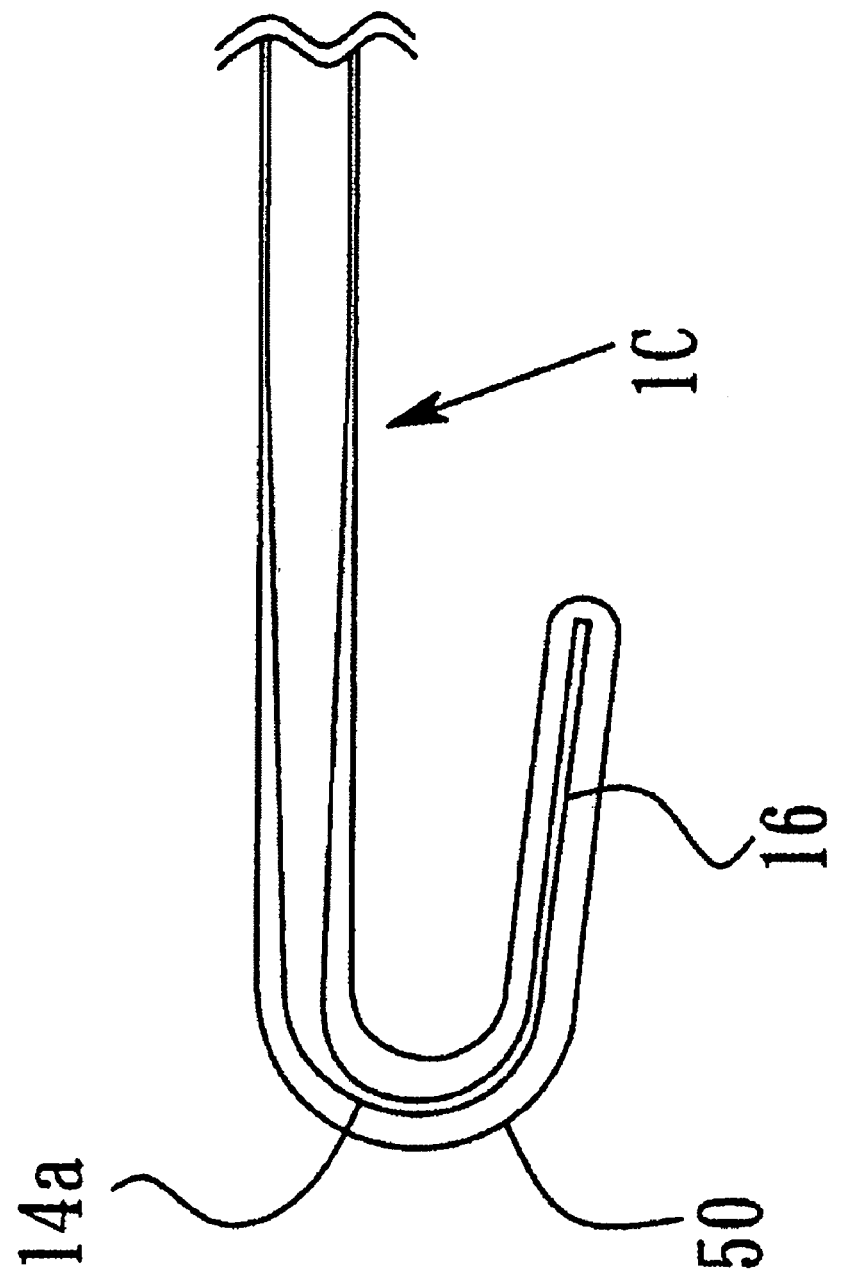
FIG. 4 is a sectional view showing a further embodiment of the medical guide wire according to the present invention.
Figure 5:
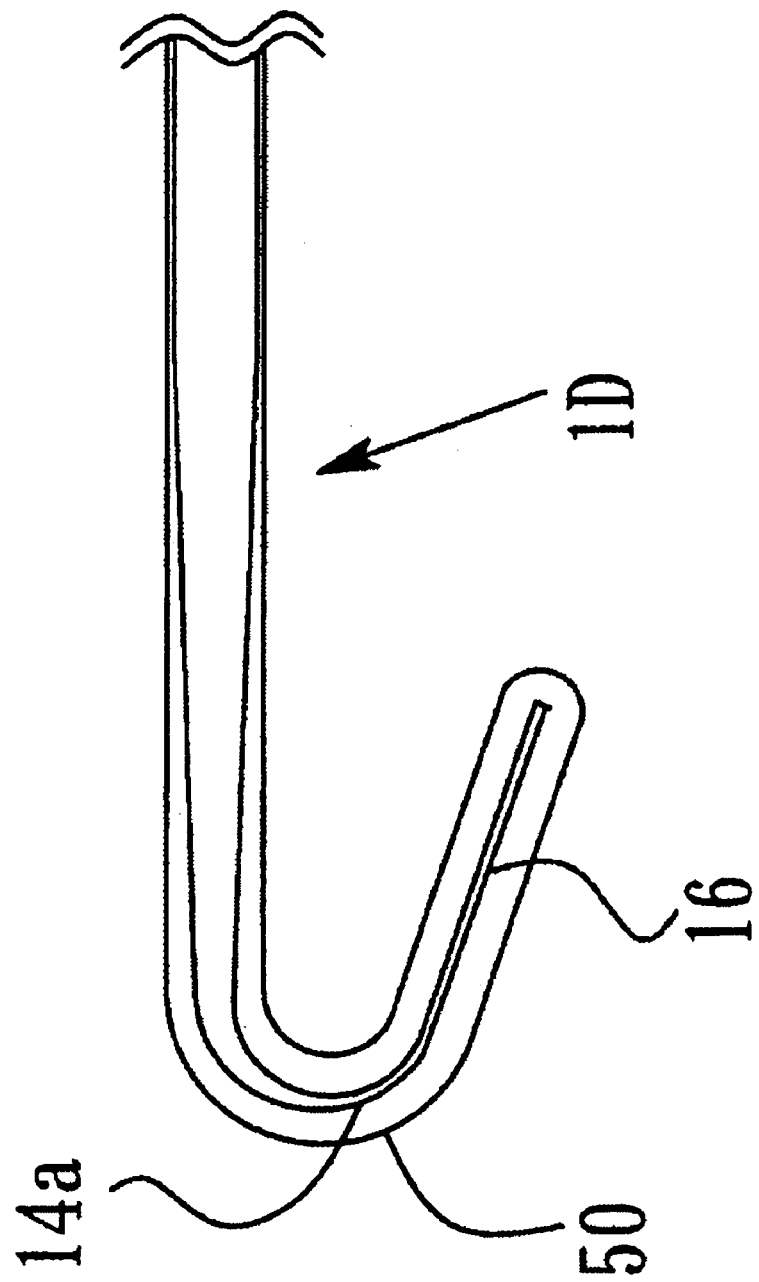
FIG. 5 is a sectional view showing yet another embodiment of the medical guide wire according to the present invention.

FIG. 3 shows another embodiment in which the taper start portion 14*a* is located between a distal portion and a proximal portion of the curved portion of the distal shape portion 50. In this guide wire 1B, the taper start portion 14*a* is located on the proximal side relative to the apex T of the distal shape portion 50 and on the distal side relative to the proximal portion of the curved portion. Also, in a guide wire 1C shown in FIG. 4, the taper start portion 14*a* is provided on the proximal side relative to the apex T of the distal shape portion 50 and on the distal side relative to the proximal portion of the curved portion. In a guide wire 1D shown in FIG. 5, the taper start portion 14*a* is located on the distal side relative to the apex T of the distal shape portion 50 and on the proximal side relative to the distal portion of the curved portion.

As for the flexural strength in the medical guide wire according to the present invention, the flexural strength at 30 mm on the proximal side from the apex of the distal shape portion 50 in the medical guide wire 1A is preferably not less than 1.5 gf, more preferably not less than 2.0 gf. If the flexural strength is less than 1.5 gf, it becomes impossible for the distal shape portion 50 to defeat the pushing resistance arising from the spreading and extension of the J-shaped portion in the beginning stage of insertion into a catheter or the like, so that it is necessary to frequently re-hold the guide wire, leading to a troublesome operation, which naturally is unfavorable. The flexural strength is determined as follows. Namely, the flexural strength is determined as an average of three measurements of the maximum load obtained when the position of 50 mm from the apex of the distal shape portion in the guide wire is fixed horizontally and the position of 30 mm from the apex of the distal shape portion is pushed down by 2 mm at a rate of 5 mm/min.

The spreading load for the distal shape portion in the medical guide wire according to the present invention is preferably not more than 15 gf, more preferably not more than 10 gf, and further preferably in the range of 6 to 10 gf. If the spreading load for the distal shape portion is greater than 15 gf, the crossability of the guide wire inside the small lumen of a catheter or the like is worsened, and the danger at the time of withdrawal of the guide wire (the load exerted on the branch portion at the time of withdrawal of the guide wire with its distal portion hooked on a branch blood vessel) is enlarged, which is unfavorable. The spreading load on the distal shape portion can be determined as an average of three measurement of the maximum load obtained when the distal shape portion is drawn into a polyethylene tube with an inside diameter of 2 mm at a rate of 5 mm/min.

The distal shape portion 50 in the medical guide wire 1A has the curved portion, and the radius of curvature of the curved portion, denoted by r in FIG. 1, is preferably in the range of 1 to 3 mm, more preferably 1.5 to 2 mm. In many cases where the puncture location is radial, the inside diameter of the blood vessel is 3 to 5 mm. Therefore, if the radius of curvature is greater than 3 mm, the resistance inside the blood vessel is enlarged, whereby steerability of the guide wire is worsened, and there arises the possibility of damaging the blood vessel wall by pushing and spreading the blood vessel wall, which naturally is unfavorable. Besides, as the radius of curvature is reduced, it becomes more difficult for the guide wire to be hooked on an inlet portion at the time of insertion thereof into a catheter or the like, and the insertability of the guide wire tends to be lowered. Thus, the radius of curvature is preferably not less than 1 mm.

The opening angle of the distal shape portion 50 in the medical guide wire according to the present invention is denoted by b as shown in FIG. 1. The opening angle is preferably in the range of 0 to 30°, more preferably 10 to 20°. Like in the case of the radius of curvature, as the opening angle of the distal portion is smaller, it becomes more difficult for the guide wire to be hooked on an inlet portion at the time of insertion thereof into a catheter or the like, and the steerability of the guide wire tends to be lowered. If the opening angle is smaller than 0°, the steerability is extremely worsened, which is unfavorable. On the other hand, as the opening angle is greater, the insertability is enhanced more. However, if the opening angle is greater than 30°, the possibility of scratching the blood vessel wall is enhanced because the angle of the guide wire distal portion against the blood vessel wall becomes greater, and the possibility of damaging the blood vessel wall is increased because the guide wire distal portion is more liable to be hooked on a branched blood vessel at the time of withdrawal. For example, the opening angle is 20° in the embodiments shown in FIGS. 1 and 5, while the opening angle is 10° in the embodiments shown in FIGS. 3 and 4.

Examples of the material used for the core wire 10 in the present invention include metallic materials such as Ni—Ti based alloys, stainless steel, etc., and synthetic resins. While any of the materials having properties suitable for the use may be appropriately selected and used, the Ni—Ti based alloys are preferred in view of pliability.

The distal portion 12 of the core wire 10 is covered by the cover portion 30. While the core wire 10 is entirely covered by the cover portion 30 in the guide wire 1A, embodiments may be adopted in which the cover portion 30 is provided only on the distal portion 12. Besides, as will be described later, an embodiment may be adopted in which the distal portion 12 of the core wire 10 is covered with a resin capable of being subjected to hydrophilic coating, and the proximal portion is covered with other resin such as silicones and fluoro-resins.

As the resin material forming the cover portion 30, a polymeric material having such a degree of flexibility as not to hinder the curving of the core wire 10 is used, in view of the covering property for the core wire 10 and the need to apply a lubricant coating to the outside surface of the resin. Examples of the polymeric material include polyurethane, polyamide elastomers, polyester elastomers, polyolefin elastomers, and polymer alloys containing a fluorine- or chlorine-containing polymer as a main constituent. In addition, the outside surface is molded to be smooth to such an extent as not to cause troubles in operation inside a blood vessel. Besides, particulates of a metal high in radiopaqueness, such as tungsten, bismuth, and barium, can be mixed into the cover material.

The outside surface of the cover material is coated with a hydrophilic polymer, for reducing the frictional resistance between it and the inside surfaces of a guide needle, a catheter and a sheath and, further, between it and the blood vessel inside wall and for realizing good steerability.

As the hydrophilic material, there can be used polymers having a multiplicity of hydrophilic groups, such as vinyl ether-maleic anhydride copolymer, vinyl ether-maleic anhydride copolymer salts, polyethers, polyacrylates, polymethacrylates, and polyvinylpyrrolidone.

Now, the present invention will be described below referring to Examples.

As the core wire 10, an Ni—Ti alloy core wire was produced in which the core wire diameter variation rate ($\alpha$) was 40%, the distal flexible portion 16 was circular in cross section, had an outside diameter ($\phi$1) of 0.11 mm, had a length of about 12 mm, and had an outside diameter substantially constant along the longitudinal direction thereof, the taper start portion 14a was located at the apex of the distal shape portion 50, and the distal shape portion 50 was J-shaped with an opening angle b of about 20° and a radius of curvature of 2 mm. Thereafter, the outside surface of the core wire was coated with a urethane resin and, further, a lubricating coating was applied thereto, to produce a medical guide wire with a proximal portion outside diameter of 0.85 mm. This guide wire was referred to as Example 1. The guide wire had a flexural strength of 1.8 gf and a spreading load of 8.8 gf.

As Examples 2 and 3, guide wires having the same materials and structure as those in Example 1, except the core wire diameter variation rates $\alpha$ were respectively 55% and 47%, were produced. The guide wires in Examples 2 and 3 had respective flexural strengths of 3.3 gf and 2.8 gf and respective spreading loads of 13.2 gf and 10.6 gf.

As Comparative Example 1, a guide wire having the same materials and structure, except for a core wire diameter variation rate $\alpha$ of 33%, was produced. Also, as Comparative Example 2, a guide wire which had a core wire diameter variation rate $\alpha$ of 20% and in which the taper start portion was located not at the distal shape portion but at 30 mm to the proximal side from the apex of the distal shape was produced. Further, as Comparative Example 3, a guide wire having the same materials and structure as those in Example 1 except for a core wire diameter variation rate $\alpha$ of 66% was produced. The guide wires in Comparative Examples 1 to 3 had respective flexural strengths of 1.3 gf, 0.6 gf, and 4.0 gf and respective spreading loads of 6.7 gf, 4.5 gf, and 15.5 gf.

A test for comparison of insertability was conducted as follows. An arbitrary position on the proximal side relative to the distal shape portion of the medical guide wire is held, and the maximum distance from the apex of the distal shape portion to the holding position such as to enable the insertion of the guide wire into a 4-Fr angiography catheter was measured three times. As a result, the average of the measured maximum distance was 8 cm in Example 1, 10 cm in Example 2, and 9 cm in Example 3.

In the medical guide wire according to this embodiment, the taper end portion of the core wire is located at a position of about 70 mm from the apex of the distal shape, which means that if $\alpha$ is not less than 40%, the guide wire can be inserted into a catheter or the like even in the condition where a shaft portion corresponding to a uniform hardness (stiffness) of the guide wire is held. Since the distal portion of the guide wire is extremely high in flexibility and is a delicate portion determining the slidability of the guide wire in a blood vessel, the large reduction in the burden on the operations, such as frequent re-holding, in the beginning stage of insertion of the guide wire has a great clinical significance.

The same measurement was carried out for the guide wire in Comparative Example 1. The average of the maximum distance was 5 cm, and buckling tended to occur due to flexion of a portion at about 3 cm from the apex of the distal shape portion in the beginning stage of insertion, and the re-holding operation was somewhat troublesome. As for the guide wire of Comparative Example 2, the average of the maximum distance was 2 cm, and the re-holding operation in the beginning stage of insertion was more troublesome. As for the guide wire of Comparative Example 3, the average of the maximum distance was 12 cm.

Next, a torsion test was conducted in the following manner. After the cover was removed from the guide wire, the distal portion of the core wire was fixed, the core wire was continuously twisted in the same direction while exerting a load of 200 gf at a span of 50 cm, and the number of twistings made until rupture of the core wire (torsional rupture strength) was measured three times.

As for the core wire in Example 2, the torsional rupture strength was 9 on average, and was 7 at minimum. Of various types of guide wires which have hitherto been used in the medical field, the one showing the lowest torsional rupture strength is on the same level as the guide wire in this example. In consideration of practical use, it is considered to be necessary for the core wire "not to be broken even when twisted five times in the same direction". Therefore, the core wire in this example can be said to be on an allowable level as to torsional rupture strength. On the other hand, the core wire in Comparative Example 3 showed a torsional rupture strength of 6 on average, and 4 at minimum; in consideration of practical use, this core wire can be said not to be on the allowable level as to torsional rupture strength.

Next, the guide wire of Example 2 was inserted into a silicone tube with an inside diameter of 3 mm prepared on the presumption of a lower arm portion through a 6-Fr sheath, and the behavior of the guide wire was confirmed. As a result, it was found that while the guide wire proceeds inside the tube with the J shape spread and extended, the J-shaped distal portion smoothly proceeded in parallel to the wall of the tube, so that the tipmost end portion would not scratch the wall. Further, since the distal portion of the guide wire proceeds over a Y-shaped branch portion (an inlet portion had a major diameter of about 4 mm) arranged supposing a blood vessel branch, so that the distal portion would not erroneously enter into a branch tube.

Next, the behavior of a blood vessel model using the guide wire of Comparative Example 3 was found to be roughly the same as in Example 2, but the feeling of resistance during pushing of the guide wire into the catheter was greater. From this it was confirmed that the steerability of the guide wire is worsened when the wire diameter variation rate at the tapered portion is excessively large.

Next, a yet further embodiment of the guide wire according to the present invention will be described below referring to FIGS. 6 and 7.

Figure 6:
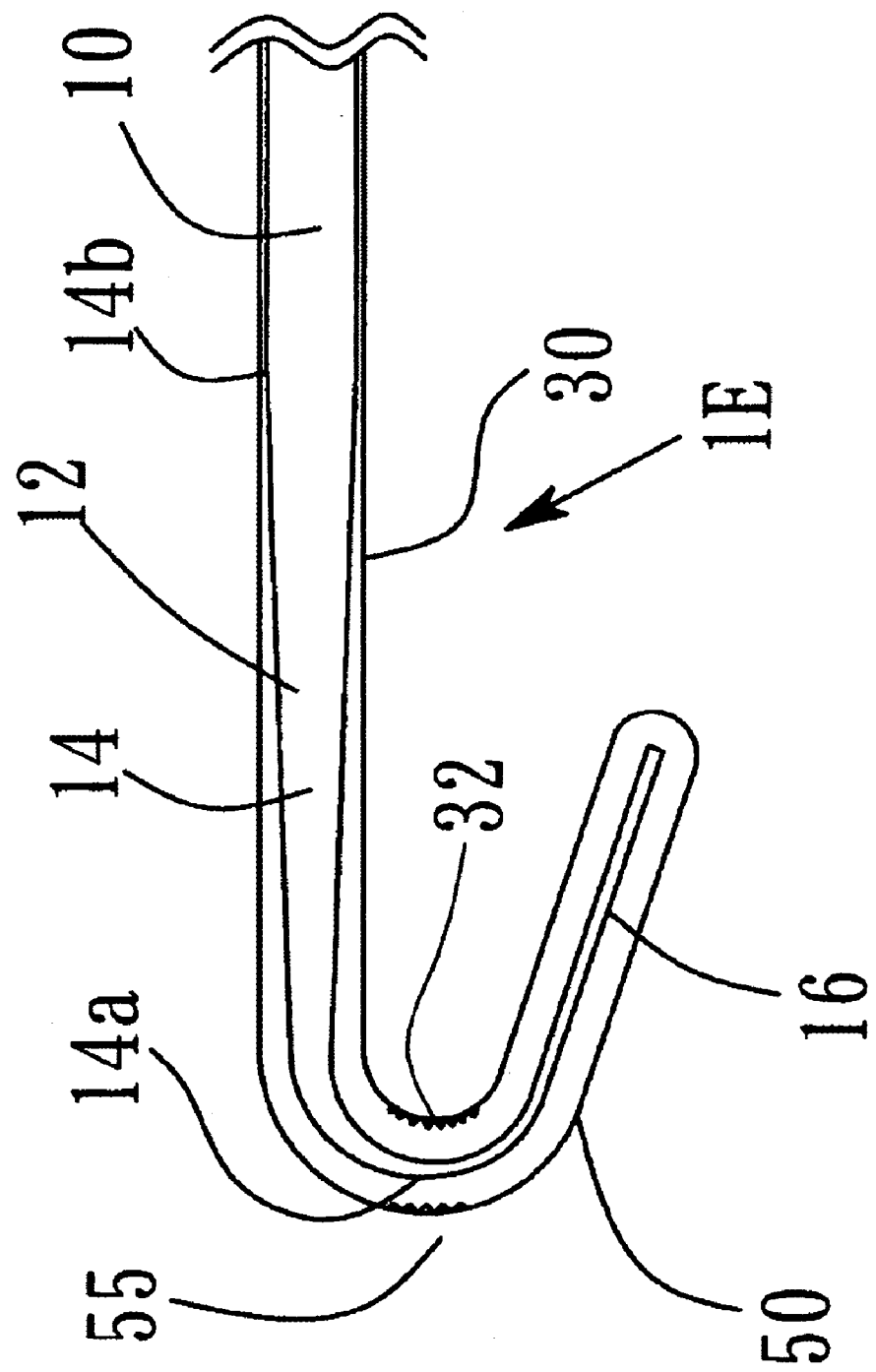
FIG. 6 is a sectional view showing a yet further embodiment of the medical guide wire according to the present invention.
Figure 7:
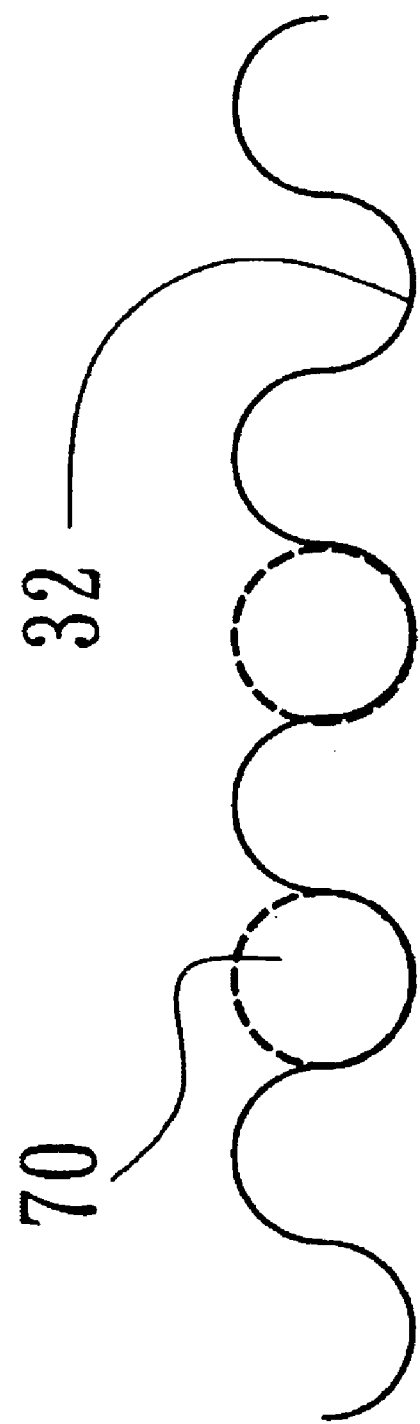
FIG. 7 is an enlarged partial end view of FIG. 6.

A guide wire 1E shown in FIG. 6 has a configuration in which the surface of a cover portion 30 at least on the inside of a curved portion 55 is provided with a groove 32 in a direction roughly orthogonal to the axial direction. The groove 32 is provided in a spiral form. The groove 32 is formed along the entire circumference of the surface of a cover portion 30 at the curved portion 55. The groove 32 is provided only in the surface of the cover portion 30 at the curved portion 55. The longitudinal section of the groove 32 is wavy, as shown in FIG. 7. The wavy groove 32 can be obtained, for example, by winding a wire around the cover portion 30 at intervals corresponding to the outside diameter of the wire, followed by heating.

The groove 32 may be annular, instead of spiral, in shape. A slit may be provided in place of the groove 32. The groove 32 may be provided only in the surface of the cover portion 30 on the inside of the curved portion 55. The groove 32 may be provided in the surface of the cover portion 30 at a distal shape portion 50 inclusive of the curved portion 55.

Now, still another embodiment of the guide wire according to the present invention will be described below referring to FIGS. 8 and 9.

Figure 8:
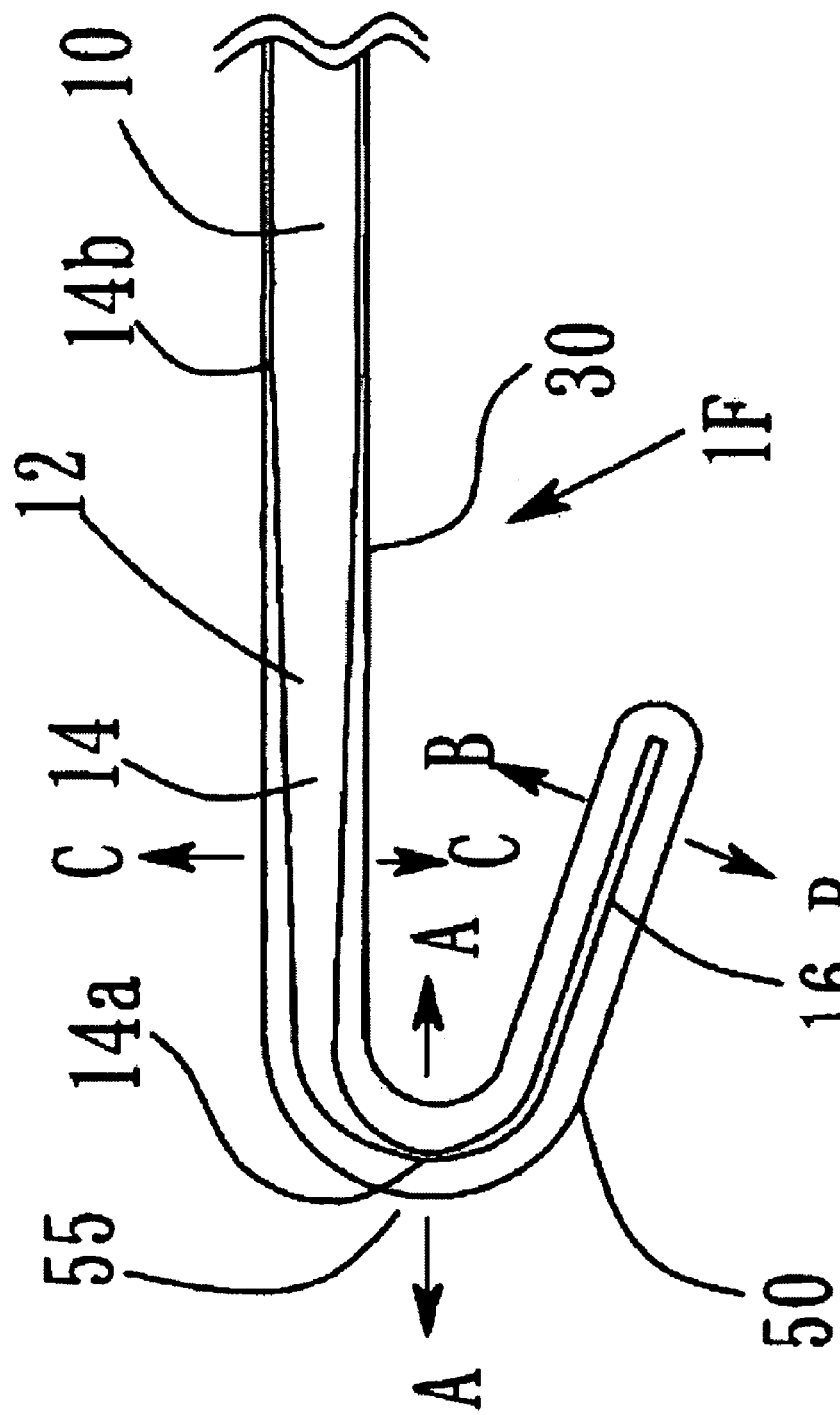
FIG. 8 is a sectional view showing a still another embodiment of the medical guide wire according to the present invention.
Figure 9:
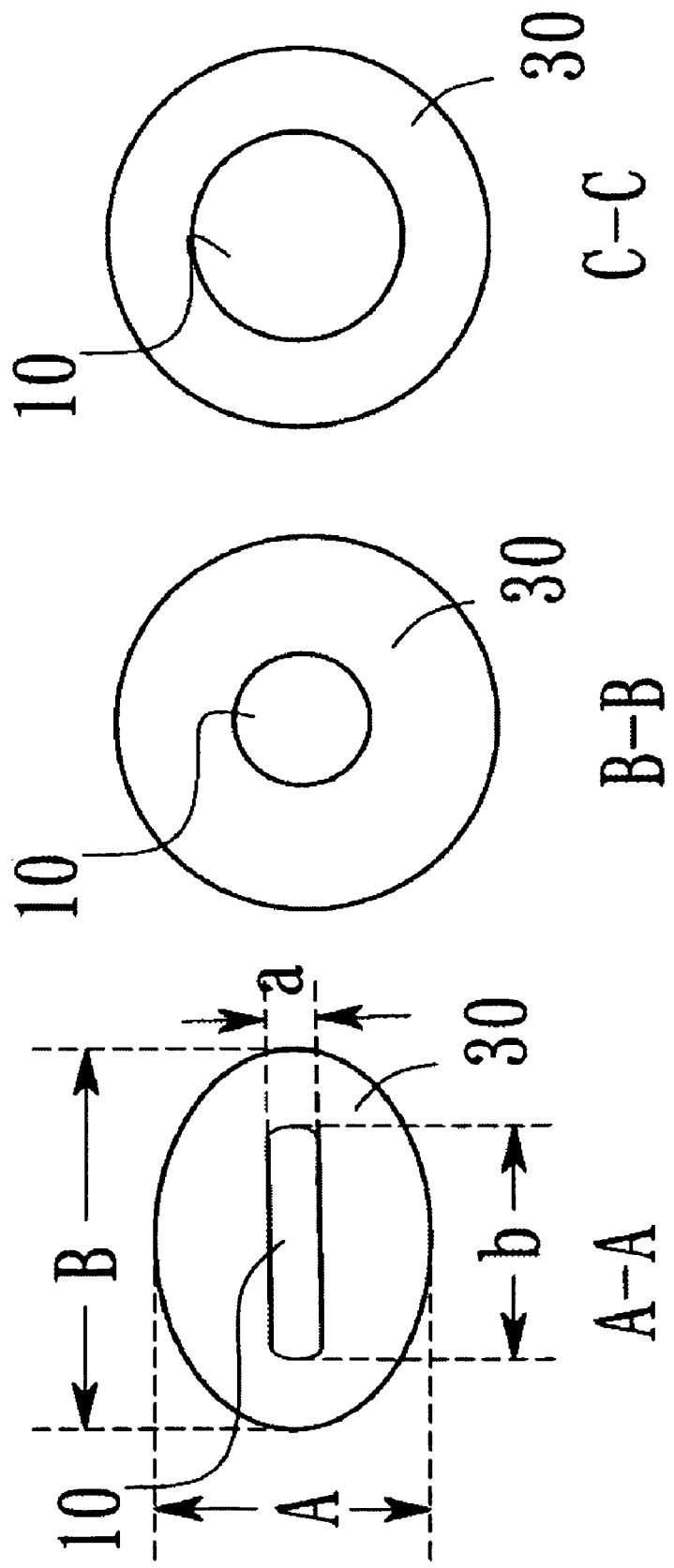
FIG. 9 is an enlarged partial end view of FIG. 8.

A guide wire 1F shown in FIG. 8 has a configuration in which, of a core wire 10 at a curved portion 55, the thickness in the direction of the radius of curvature of a curved portion 55 is smaller than the thickness in the direction orthogonal to the radius-of-curvature direction. The upward direction in FIG. 9 is the leftward direction in FIG. 8, and represents the direction of the radius of curvature of the curved portion 55. As shown in A-A end view in FIG. 9, of the core wire 10 at the curved portion 55, the thickness in the radius-of-curvature direction is smaller than the thickness in the direction orthogonal to the radius-of-curvature direction. The core wire 10 at the curved portion 55 is preferably flat in cross section. The cross section of the core wire 10 at the curved portion 55 may, for example, have a minor axis a of 0.05 mm and a major axis b of 0.19 mm. In the cross section of the cover portion 30 at the curved portion 55, the thickness in the radius-of-curvature direction of the curved portion 55 is smaller than the thickness in the direction orthogonal to the radius-of-curvature direction. Of the curved portion 55, for example, the thickness A in the radius-of-curvature may be 0.79 mm, and the thickness B in the direction orthogonal to the radius-of-curvature direction may be 0.88 mm. As shown in B-B end view of FIG. 9, the core wire 10 at a distal flexible portion 16 is roughly circular in cross section. The diameter may, for example, be 0.11 mm. It is preferable for the cross-sectional area of the flat core wire 10 to be roughly equal to the circular cross-sectional area of the core wire 10 at the distal flexible portion 16. The cover portion 30 at the distal flexible portion 16 is roughly circular in cross section. As shown in C-C end view in FIG. 9, the core wire 10 at a tapered portion 14 is roughly circular in cross section. The cross-sectional area of the core wire 10 at the tapered portion 14 is preferably greater than the cross-sectional area of the core wire 10 at the distal flexible portion 16. The cover portion 30 at the tapered portion 14 is roughly circular in cross section. The cross-sectional areas of the cover portion 30 and the core wire 10 at the tapered portion 14 are preferably greater than the cross-sectional areas of the cover portion 30 and the core wire 10 at the distal flexible portion 16. The cross-sectional areas of the cover portion 30 and the core wire 10 at the curved portion 55 are preferably smaller than the cross-sectional areas of the cover portion 30 and the core wire 10 at the distal flexible portion 16.

Now, a still further embodiment of the guide wire according to the present invention will be described below referring to FIGS. 10 and 11.

Figure 10:
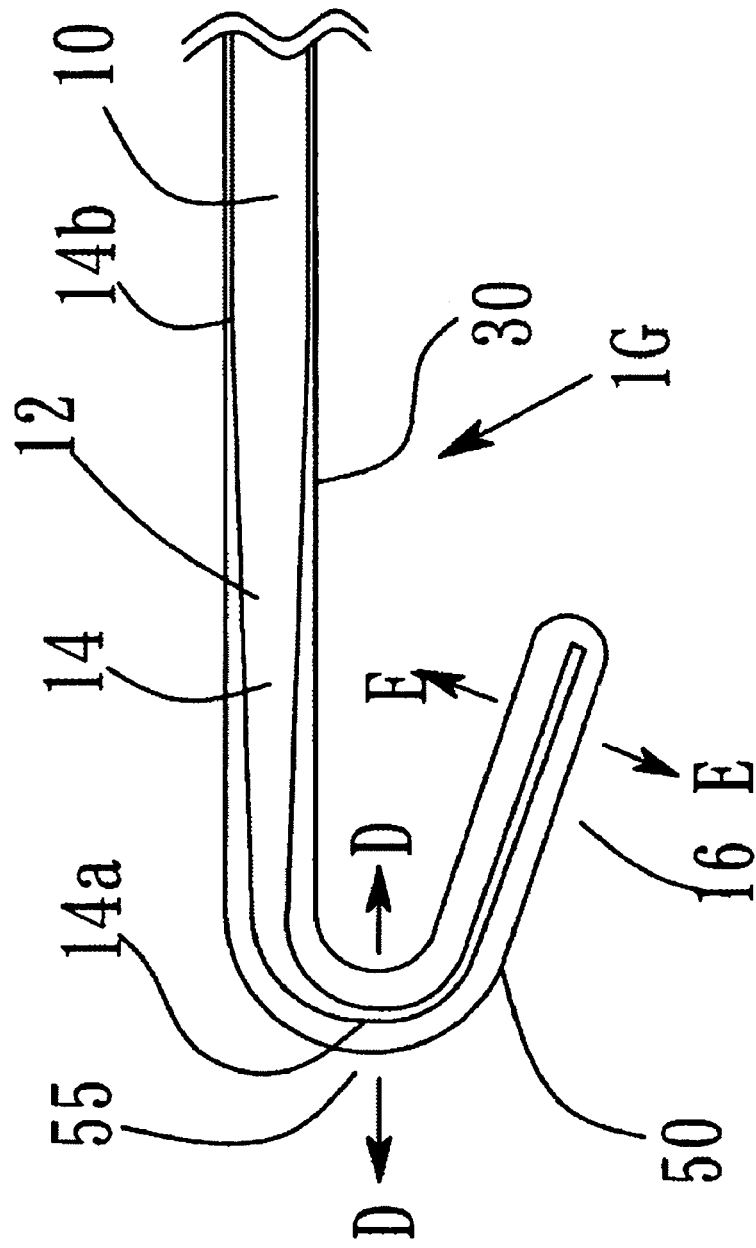
FIG. 10 is a sectional view showing a still further embodiment of the medical guide wire according to the present invention.
Figure 11:
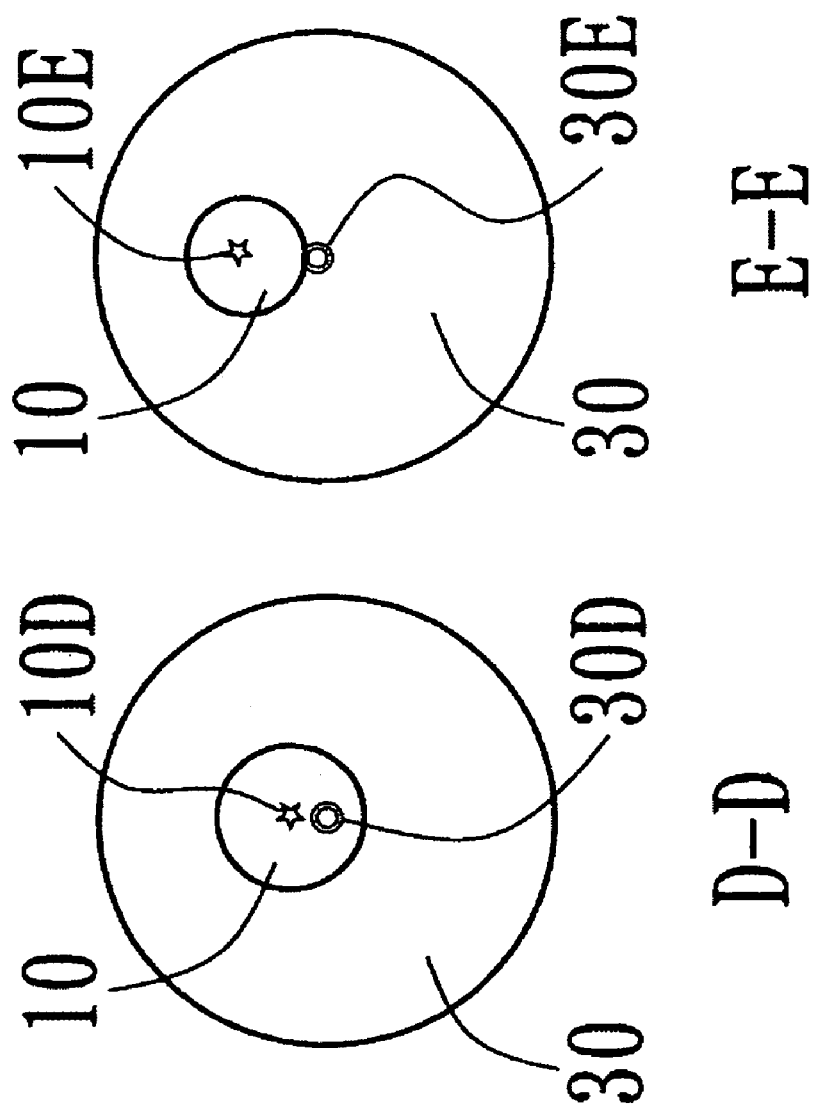
FIG. 11 is an enlarged partial end view of FIG. 10.

In the guide wire 1G shown in FIG. 10, the cross-sectional center point of a core wire 10 at a distal shape portion 50 and the cross-sectional center point of a cover portion 30 are located at different positions. The upward direction in FIG. 11 is the leftward direction in FIG. 10, and represents the direction of the radius of curvature of a curved portion 55. As shown in D-D end view in FIG. 11, both the core wire 10 and the cover portion 30 are roughly circular in cross section. The cross-sectional center 10D (represented by "☆") of the core wire 10 is deviated from the cross-sectional center point 30D (represented by "⊙") of the cover portion 30 in the direction of the radius of curvature of the curved portion 55. The thickness of the cover portion 30, in relation to the core wire 10, is greater on the inside (the lower side in FIG. 11) of the curved portion 55 than on the outside (the upper side in FIG. 11) of the curved portion 55. The cross-sectional center point 30D of the cover portion 30 is preferably located in the cross section of the core wire 10. As shown in E-E end view in FIG. 11, the cross-sectional center point 10E (represented by "☆") of the core wire 10 is deviated from the cross-sectional center point 30E (represented by "⊙") of the cover portion 30 in the direction of the radius of curvature of the curved portion 30. The cross-sectional center point 30E of the cover portion 30 is preferably located in the outside of the cross section of the core wire 10.

In the present invention, the characteristic features of the guide wires 1A to 1G may be adopted in combination. For example, the guide wire in which the core wire 10 at the curved portion 55 is smaller in thickness in the direction of the radius of curvature of the curved portion 55 may be so configured that the cross-sectional center point of the core wire 10 at the distal shape portion 50 and the cross-sectional center portion 30 of the cover portion 30 are located at different positions. In addition, one of the characteristic features of the guide wires 1A to 1C may be combined with one or a plurality of the characteristic features of the guide wires 1F and 1G.

The guide wire according to the present invention can be used for introducing a medical implement, such as a catheter and a sheath, to a target location in the region of chest, abdominal region or the like through a radial, brachial or femoral portion, and its adaptation range is not limited by the puncture location or the target location.

The present invention is not limited to the details of the above described preferred embodiments. The scope of the invention is defined by the appended claims and all changes and modifications as fall within the equivalence of the scope of the claims are therefore to be embraced by the invention.

What is claimed is:

1. A medical guide wire comprising a core wire having a distal portion, and a cover portion formed of a resin covering at least said distal portion of said core wire, said guide wire provided with a distal shape portion having a curved portion, the curved portion having a distal end and a proximal end, the curved portion continuously curving from the distal end of the curved portion to the proximal end of the curved portion, and the distal shape portion possessing an opening angle of 0° to 30°, wherein said distal portion of said core wire comprises a tapered portion continuously varied in outside diameter, and a distal flexible portion provided on the distal side of said tapered portion and more flexible than said tapered portion, and said tapered portion possessing a wire diameter variation rate of 40 to 55%, and wherein said tapered portion has a tapered start portion at which an increase in the outside diameter toward the proximal side is started and a tapered end portion at which the increase in the outside diameter ends, and said start portion is located at an apex of said curved portion of said distal shape portion.

2. The medical guide wire as set forth in claim 1, wherein said distal flexible portion is substantially circular in cross section, and has a diameter of 0.08 to 0.13 mm.

3. The medical guide wire as set forth in claim 1, wherein a spreading load of said distal shape portion representing a force required to spread said distal shape portion is not more than 15 gf.

4. The medical guide wire as set forth in claim 1, wherein a surface of said cover portion on at least an inside of said curved portion is provided with a groove substantially orthogonal to an axial direction.

5. The medical guide wire as set forth in claim 1, wherein said core wire at said curved portion is flat.

6. The medical guide wire as set forth in claim 1, wherein, in said distal shape portion, a cross-sectional center point of said core wire and a cross-sectional center point of said cover portion are located at different positions.

7. A medical guide wire comprising a core wire having a distal portion, and a cover portion formed of a resin for covering at least said distal portion of said core wire, said guide wire provided with a distal shape portion having a curved portion, the curved portion having a distal end and a proximal end, the curved portion continuously curving from the distal end of the curved portion to the proximal end of the curved portion, and the distal shape portion possessing an opening angle of 0° to 30°, wherein said distal portion of said core wire comprises a tapered portion continuously varied in outside diameter and having a tapered start portion and a tapered end portion at which increases in the outside diameter of the core wire ends, the tapered start portion being located at said curved portion of said distal shape portion, and a distal flexible portion provided on the distal side of said tapered portion; and said start portion being located at an apex of said curved portion.

8. The medical guide wire as set forth in claim 7, wherein said distal flexible portion is substantially circular in cross section, and has a diameter of 0.08 to 0.13 mm.

9. The medical guide wire as set forth in claim 7, wherein said tapered portion possesses a wire diameter variation rate of 40 to 55%.

10. The medical guide wire as set forth in claim 7, wherein a spreading load of said distal shape portion representing a force required to spread said distal shape portion is not more than 15 gf.

11. The medical guide wire as set forth in claim 7, wherein a surface of said cover portion on at least an inside of said curved portion is provided with a groove substantially orthogonal to an axial direction.

12. The medical guide wire as set forth in claim 7, wherein said core wire at said curved portion is flat.

13. The medical guide wire as set forth in claim 7, wherein, in said distal shape portion, a cross-sectional center point of said core wire and a cross-sectional center point of said cover portion are located at different positions.

14. A medical guide wire comprising a core wire having a distal portion, and a cover portion formed of a resin covering at least said distal portion of said core wire, said guide wire provided with a distal shape portion having a curved portion, the curved portion continuously curving, wherein said distal portion of said core wire comprises a tapered portion continuously varied in outside diameter, the tapered portion having a start portion at which the outside diameter begins to vary, the start portion being located in a vicinity of a position corresponding to a most projected portion when viewed from the proximal side toward the distal side, the distal shape portion comprising a first leg portion which merges into the curved portion and a second leg portion into which the curved portion merges so that the second leg portion is located distally of the first leg portion, the curved portion being configured to form an internal angle of 0° to 30° between the first leg portion and the second leg portion, and said start portion being located at an apex of said curved portion.

15. The medical guide wire as set forth in claim 14, wherein the core wire possesses an outside surface, the cover portion contacting the outside surface of the core wire at least over the distal portion of the core wire.

16. The medical guide wire as set forth in claim 14, wherein a spreading load of the distal shape portion representing a force required to spread the distal shape portion is not more than 15 gf.

17. A medical guide wire comprising a core wire having a distal portion, and a cover portion formed of a resin covering at least said distal portion of said core wire, said guide wire provided with a distal shape portion having a curved portion, the curved portion having a distal end and a proximal end, the curved portion continuously curving from the distal end of the curved portion to the proximal end of the curved portion, and the curved portion possessing a radius of curvature of 1 mm to 3 mm, wherein said distal portion of said core wire comprises a tapered portion continuously varied in outside diameter, and a distal flexible portion provided on the distal side of said tapered portion and more flexible than said tapered portion, and said tapered portion possessing a wire diameter variation rate of 40 to 50%, and wherein said tapered portion has a tapered start portion at which an increase in the outside diameter toward the proximal side is started and a tapered end portion at which the increase in the outside diameter ends, and said start portion is located at an apex of said curved portion of said distal shape portion.

* * * * *